United States Patent
Krainiak et al.

[11] Patent Number: 6,010,400
[45] Date of Patent: Jan. 4, 2000

[54] ISOLATION WORKSTATION

[75] Inventors: Russell Edward Krainiak, Washington; Mark Anthony Huza, Greenville, both of N.C.

[73] Assignee: Flanders Filters, Inc., Washington, N.C.

[21] Appl. No.: 08/968,050

[22] Filed: Nov. 12, 1997

Related U.S. Application Data

[62] Division of application No. 08/450,529, May 25, 1995, Pat. No. 5,711,705.

[51] Int. Cl.⁷ .................................................. B01L 1/04
[52] U.S. Cl. .............................................. 454/187; 454/57
[58] Field of Search ................................. 454/187, 191, 454/192, 56, 57

[56] References Cited

U.S. PATENT DOCUMENTS

| | | |
|---|---|---|
| Re. 33,007 | 8/1989 | Bier . |
| 3,811,250 | 5/1974 | Fowler, Jr. . |
| 3,874,754 | 4/1975 | Saunders et al. . |
| 3,895,570 | 7/1975 | Eagleson, Jr. . |
| 4,030,518 | 6/1977 | Wilcox . |
| 4,092,245 | 5/1978 | Franks ........................................ 210/64 |
| 4,118,226 | 10/1978 | Bourassa . |
| 4,157,937 | 6/1979 | Ingram, II . |
| 4,169,123 | 9/1979 | Moore et al. . |
| 4,169,124 | 9/1979 | Forstrom et al. . |
| 4,230,663 | 10/1980 | Forstrom et al. . |
| 4,249,463 | 2/1981 | Hornby . |
| 4,566,293 | 1/1986 | Arner et al. . |
| 4,854,005 | 8/1989 | Allan et al. . |
| 4,863,677 | 9/1989 | Schmidt et al. . |
| 4,863,688 | 9/1989 | Schmidt et al. ........................... 422/28 |
| 4,909,999 | 3/1990 | Cummings et al. . |
| 4,935,371 | 6/1990 | Rickloff . |
| 4,941,519 | 7/1990 | Sestak et al. . |
| 5,173,258 | 12/1992 | Childers . |
| 5,190,659 | 3/1993 | Wang et al. . |
| 5,194,078 | 3/1993 | Yonemura et al. . |
| 5,236,480 | 8/1993 | Svensson et al. . |
| 5,316,560 | 5/1994 | Krone-Schmidt et al. ............ 55/385.2 |
| 5,317,896 | 6/1994 | Sheth et al. . |
| 5,576,613 | 11/1996 | Miline . |

*Primary Examiner*—Harold Joyce
*Assistant Examiner*—Derek S. Boles
*Attorney, Agent, or Firm*—Alston & Bird LLP

[57] ABSTRACT

An isolation work station comprising an enclosure, and an air circulation system and high efficiency air filter for generating a downwardly directed laminar air flow through the enclosure. Periodic sterilization of the enclosure may be accomplished by adding a sterilant, such as vaporized hydrogen peroxide, to the airstream, and the filter is impregnated with a catalyst for degrading the vaporized hydrogen peroxide during the purge cycle and wherein the airstream is circulated at a relatively low speed so as to increase the residence time in the filter.

13 Claims, 4 Drawing Sheets

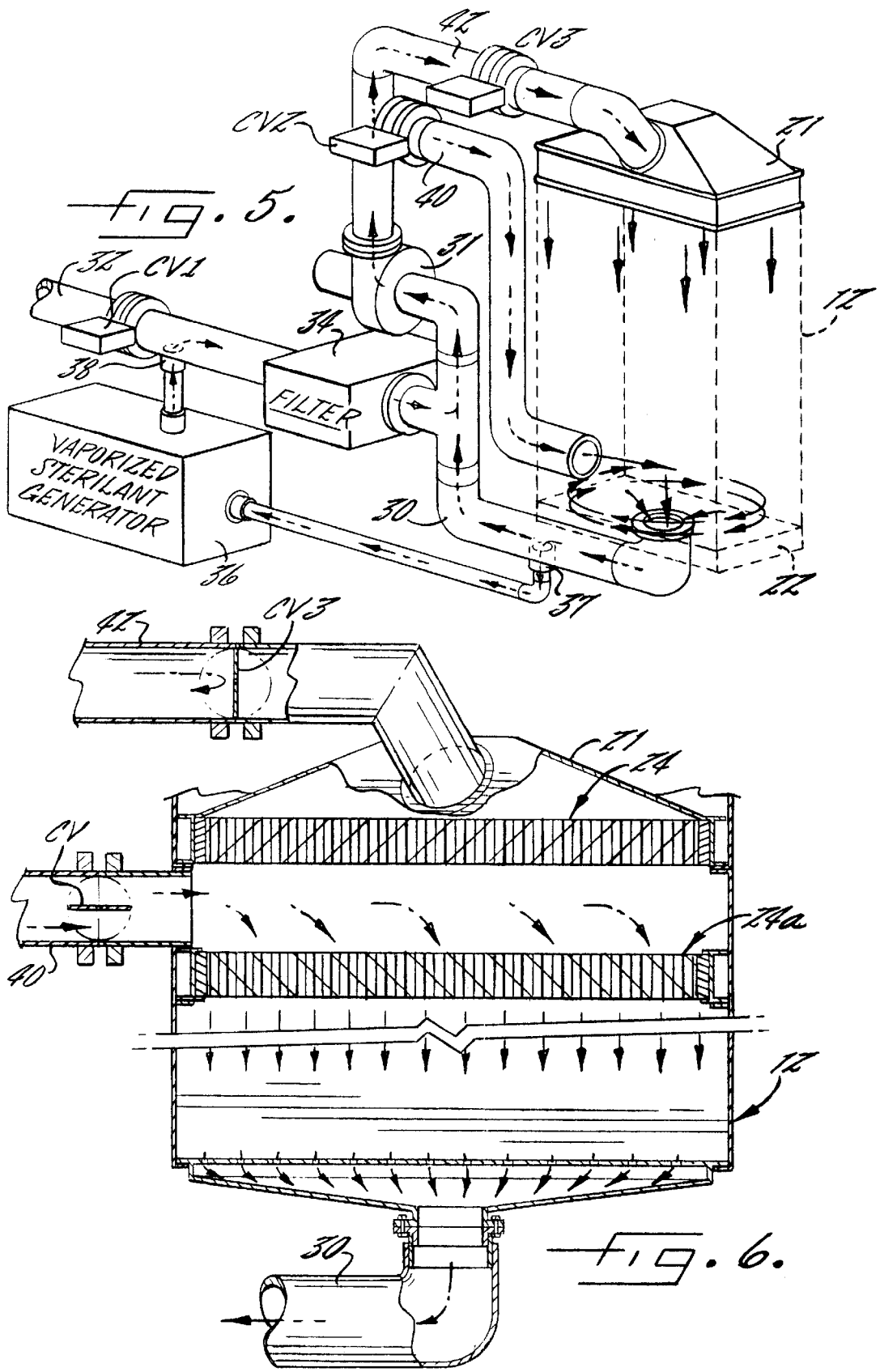

ISOLATION WORKSTATION

This application is a divisional of application Ser. No. 08/450,529, filed May 25, 1995, now U.S. Pat. No. 5,711,705.

BACKGROUND OF THE INVENTION

The present invention relates to an isolation work station suitable for providing an ultra clean work environment for the production of sterile products, drug manufacturing operations, and the like.

Work station isolators are known which comprise a generally rectangular enclosure having a glass front wall which mounts one or two flexible gloves for permitting a technician to reach through the wall and into the enclosure to perform work tasks therein and while being isolated from the environment within the enclosure. Also, in order to minimize the chances for contamination, isolators of this type commonly provide a filtered, laminar air flow downwardly through the enclosure, so as to prevent airborne contaminants from coming into contact with the sterile products being processed in the enclosure.

In the case of many manufacturing or assembly operations, it is necessary to completely sterilize the interior of the isolator between manufacturing operations, so as to prevent product contamination. As one example, the Food and Drug Administration (FDA) currently recommends that all medical and surgical products be sterilized so as to achieve a live organism count of less than one part per million in the enclosure. In order to provide such sterilization, steam or ethylene oxide treatments have been suggested, but more conventionally, the sterilization is accomplished by vaporized hydrogen peroxide which is circulated through the enclosure for a period of time, such as 10–15 minutes. A generator capable of generating vaporized hydrogen peroxide for this purpose is disclosed, for example, in U.S. Pat. Nos. 4,863,688 and 4,935,371, and such a generator is manufactured by the American Sterilizer Company of Erie, Penn. as Model No. VHP1000.

After sterilization is complete, it is necessary to then flush the residual hydrogen peroxide from the isolator, and this is typically accomplished by passing an airstream through the isolator while bleeding off a parallel stream which is passed through a granular gas type filter which contains a catalyst for degrading the residual hydrogen peroxide into moisture and oxygen, and which is located in the vaporized hydrogen peroxide generator. Since the hydrogen peroxide is absorbed by plastic, and other materials which are normally present in the isolator, it takes a significant time, typically 24 hours, for these materials to offgas the hydrogen peroxide and for the isolator to reach the required levels to permit the isolator to be reused with other products.

It is an object of the present invention to provide a work station isolator of the described type which has the capability of rapidly and efficiently purging the residual hydrogen peroxide from the isolator after the sterilization procedure.

It is a further object of the present invention to provide an isolation work station of the described type which, during the normal cycle of operation, efficiently degrades any residual hydrogen peroxide which may be released from the components of the work station after the purging cycle is completed.

SUMMARY OF THE INVENTION

The above and other objects and advantages of the present invention are achieved by the provision of an isolation work station which comprises a generally rectangular enclosure comprising upstanding front and rear side walls, and upstanding opposite end walls, and with the side walls and the end walls defining an open top and an open bottom of the enclosure. Upper and lower plenums communicate with the open top and open bottom of the enclosure respectively, and at least one high efficiency particulate air filter is sealably mounted in the upper plenum and so as to be disposed horizontally across substantially the entire area of the top of said enclosure. Also, the filter includes a sterilant degrading catalyst.

At least one flexible glove is sealably mounted in the front side wall of the enclosure, which is transparent, so as to permit a technician to reach through the front side wall and into the enclosure to perform work tasks therein and while being isolated from the environment within the enclosure. Also, an air circulation system is provided for circulating air downwardly through the filter and the enclosure and comprising a main duct extending from the lower plenum to the upper plenum at a location above the filter, and a blower positioned in the main duct for causing air to flow through the main duct from the lower plenum to the upper plenum and then through the filter and the enclosure and back to the lower plenum.

The isolation work station of the present invention preferably also comprises an air inlet duct communicating with the outside environment and with the main duct, and a first valve positioned in the air inlet duct for permitting selective flow therethrough. Further, a first port is provided which communicates with the main duct for permitting the main duct to be selectively connected to the inlet of a generator of vaporized sterilant, such as hydrogen peroxide, and second port is provided which communicates with the main duct at a location downstream of the first port for permitting the main duct to be selectively connected to the outlet of the vaporized sterilant generator.

The work station of the present invention preferably also comprises a secondary duct connected to the main duct at a location which is downstream of the second port and which communicates with the upper plenum or the enclosure at a location below the filter. A second valve is provided for permitting selective flow through the secondary duct. By this arrangement, an airstream containing the vaporized sterilant may be delivered into the enclosure of the work station and so as to circulate through the enclosure and thereby contact and bio-decontaminate surfaces within the enclosure.

In the preferred embodiment of the present invention, the filter comprises a sheet of high efficiency or "absolute" filtering media which is folded in accordion fashion upon itself to form a filter pack, and the filter media is coated or impregnated with a catalyst which rapidly degrades the sterilant during the sterilant purging cycle. Also, the catalyst bearing filter serves to protect the products within the enclosure from any offgasing sterilant which is released from the materials in the isolator after the isolator has been purged and again started to run in its normal operating cycle. Where the sterilant is hydrogen peroxide, the catalyst preferably comprises titanium oxide, which promotes the degradation of hydrogen peroxide into water vapor and oxygen, and which is generated by a smoke bomb of the type conventionally used to charge high efficiency air filters with smoke during a leak testing procedure. Thus the filter media can be coated or impregnated with titanium oxide by the same process presently employed for charging the media during a leak testing procedure. Other catalysts are known which promote the degradation of hydrogen peroxide, and other methods to coat or impregnate the filter media could be employed.

BRIEF DESCRIPTION OF THE DRAWINGS

Some of the objects and advantages of the present invention having been stated, others will appear as the description proceeds, when taken in conjunction with the accompanying drawings, in which

FIGS. 3–5 are schematic perspective views of the work station and particularly illustrating the air circulation system of the work station during normal operation, pressure decay testing, and sterilization cycles, respectively; and FIG. 6 is a view similar to FIG. 2 but illustrating a second embodiment of the work station.

BRIEF DESCRIPTION OF THE PREFERRED EMBODIMENTS

Figure 1:
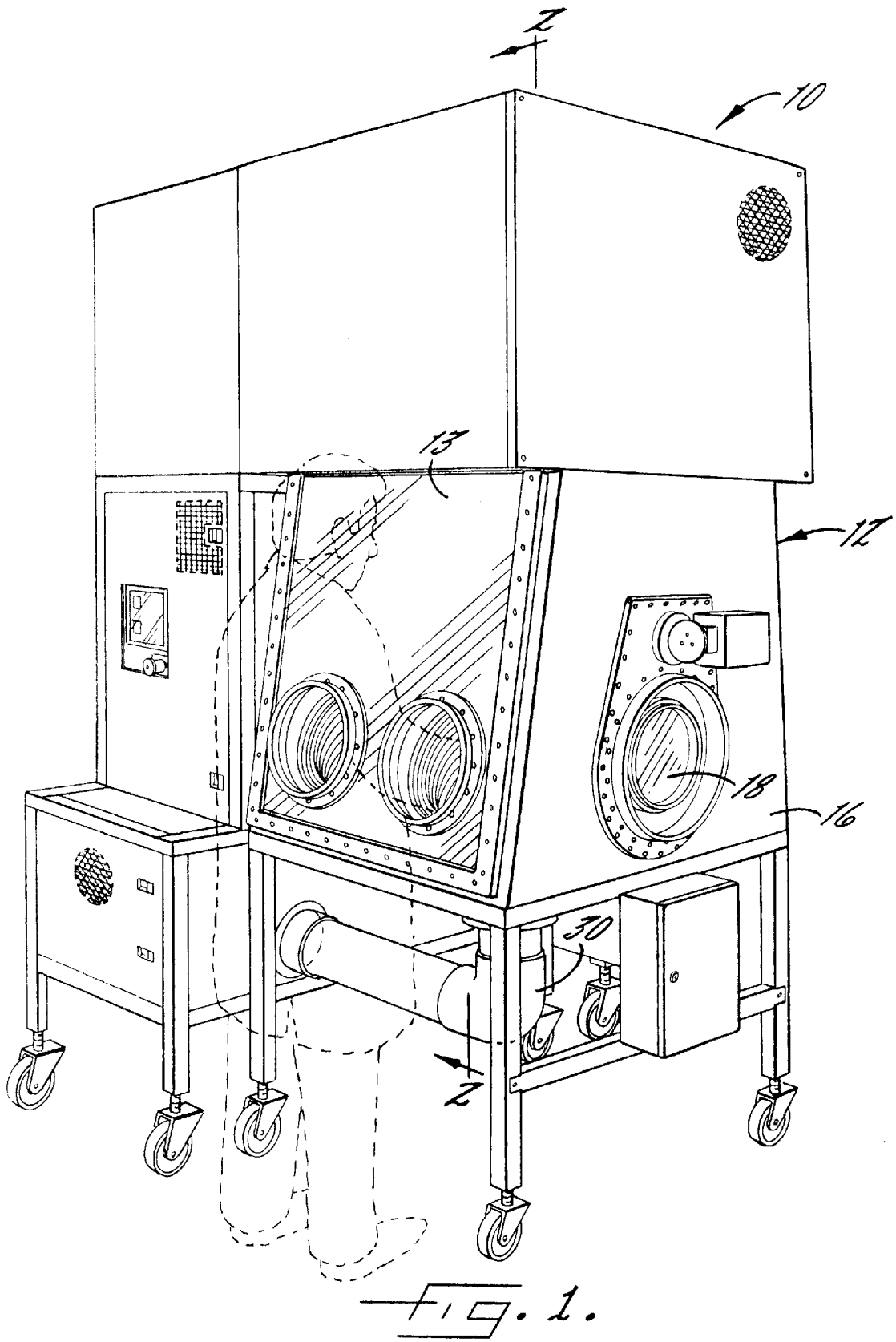
FIG. 1 is a perspective view of an isolation work station which embodies the present invention, and which illustrates the manner in which work tasks are performed by the technician while remaining isolated from the interior of the work station.
Figure 2:
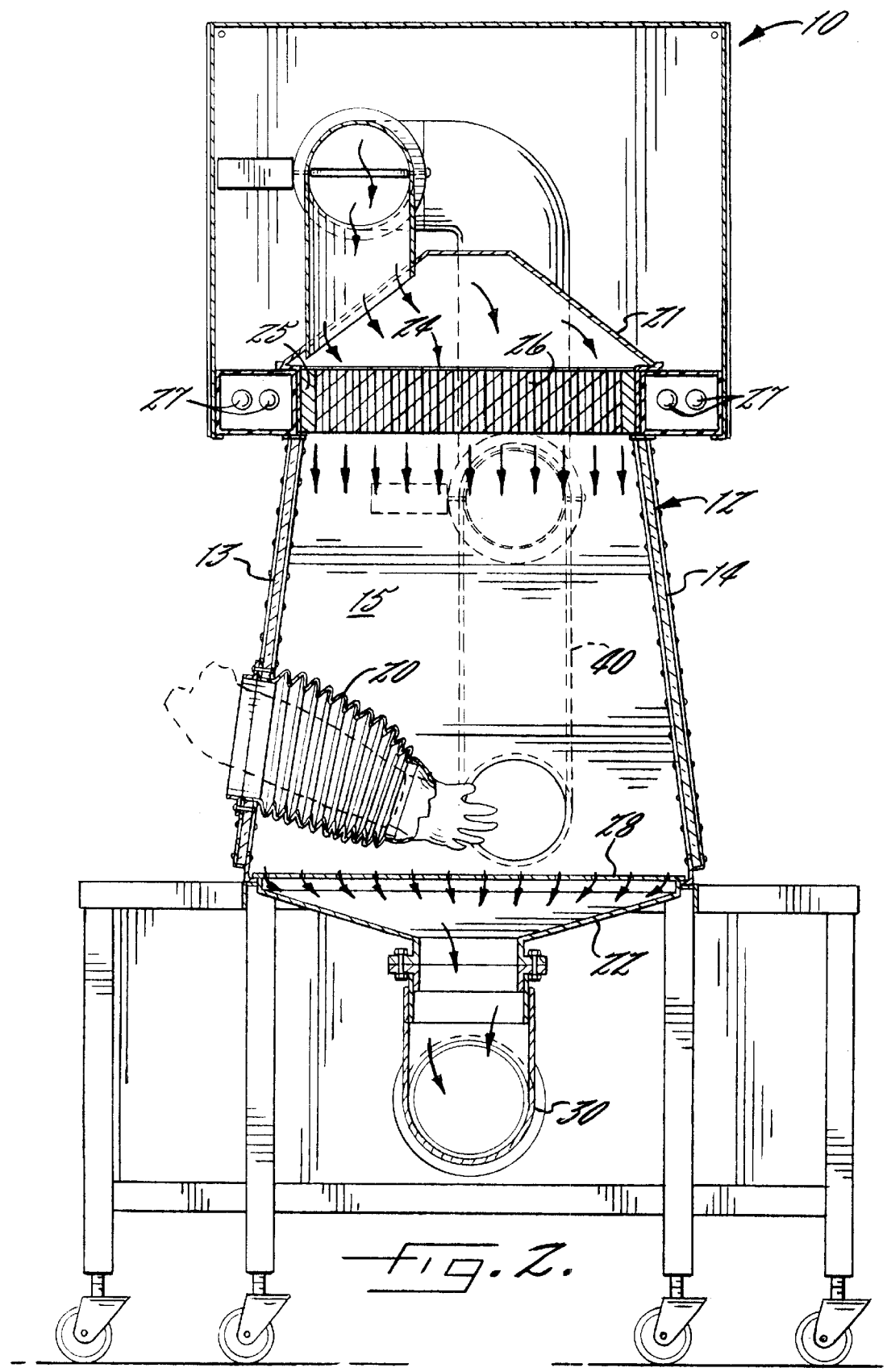
FIG. 2 is a schematic sectional view of the work station illustrated in FIG. 1.

FIGS. 1 and 2 illustrate an isolation work station 10 which embodies the present invention, and which comprises a generally rectangular enclosure 12 which includes upstanding front and rear side walls, 13, 14, and upstanding opposite end walls, 15, 16, with the side walls and end walls defining an open top and an open bottom of the enclosure. As best seen in FIG. 1, the end wall 16 includes a product entry port 18 of conventional design, and the front and rear walls 13, 14 comprise transparent glass and the front wall sealably mounts a pair of flexible gloves 20 in the conventional manner, and so as to permit a technician to reach through the front side wall and into the enclosure to perform work tasks therein, and while being isolated from the environment within the enclosure.

An upper plenum 21 communicates with the open top of the enclosure 12, and a lower plenum 22 communicates with the open bottom of the enclosure. A high efficiency particulate air filter 24 is sealably mounted in the upper plenum, and so as to be disposed horizontally across substantially the entire area of the top of the enclosure. In accordance with industry standards, the high efficiency particulate air filter 24, also commonly referred to as an "absolute" filter, comprises a rectangular frame 25 having a centrally disposed air flow opening therethrough, and a filter pack 26 sealably mounted in the frame and filling the airflow opening. The filter pack 26 comprises a sheet of filtering media folded upon itself in accordion fashion, and with the filtering media being capable of removing at least 99.9% of the submicron sized particles from the air passing therethrough. Filters of the described type are further described in U.S. Pat. Nos. 4,584,005 and 4,030,518, the disclosures of which are expressly incorporated herein by reference. Also, in accordance with the present invention, the filter media is impregnated with a catalyst, such as an oxide of titanium, in the manner and for the purposes further described below.

In the illustrated embodiment, a conventional light fixture 27 is mounted in the upper plenum 21 immediately above each of the front and rear end walls 13, 14. Also, the open bottom of the enclosure 12 mounts a perforated floor plate 28, which supports the products being processed in the enclosure while permitting air flow vertically therethrough and into the lower plenum 22.

The isolation work station 10 further comprises an air circulation system for circulating air downwardly through the filter and the enclosure in a laminar flow pattern. The air circulation system comprises a main duct 30 extending from the lower plenum 22 to the upper plenum 21 at a location above the filter 24, and a blower 31 is positioned in the main duct 30 for causing air to flow through the main duct from the lower plenum to the upper plenum and then through the filter 24 and enclosure 12 and back to the lower plenum.

An air inlet duct 32 communicates with the outside environment and with the main duct 30, and a first control valve CV-1 is positioned in the air inlet duct for permitting selective flow therethrough. Also, a high efficiency particulate air filter 34 is positioned in the air inlet duct 32 downstream of the valve CV-1.

In order to permit the air circulation system to be operatively connected to a sterilant generator 36 of the type described above, there is provided a first port 37 in the main duct for connecting to the inlet of the generator, and a second port 38 connected to the air inlet duct 32 for selectively connecting the main duct to the outlet of the generator 36. In the preferred embodiment, the generator 36 generates an airstream containing vaporized hydrogen peroxide, and may, for example, comprise the known unit manufactured by American Sterilizer Company as described above.

The air circulation system further includes a secondary duct 40 connected to the main duct 30 at a location which is downstream of the connection with the air inlet duct 32, and which communicates with the end wall 15 of the enclosure at a location below the filter 24. A second control valve CV-2 is provided in the secondary duct 40 for permitting selective flow therethrough. Also, the secondary duct 40 is preferably oriented with respect to the enclosure so as to enter the enclosure just above the floor plate 28 and in an inclined direction as seen in FIG. 5, so as to form a vortex which circulates through the enclosure and thereby contacts and sterilizes all surfaces within the enclosure.

The main duct 30 further defines a main duct segment 42 which extends from the location at which the secondary duct 40 connects to the main duct 30 and to the upper plenum 21. Also, a third control valve CV-3 is positioned in the main duct segment for permitting selective flow therethrough.

Figure 3:
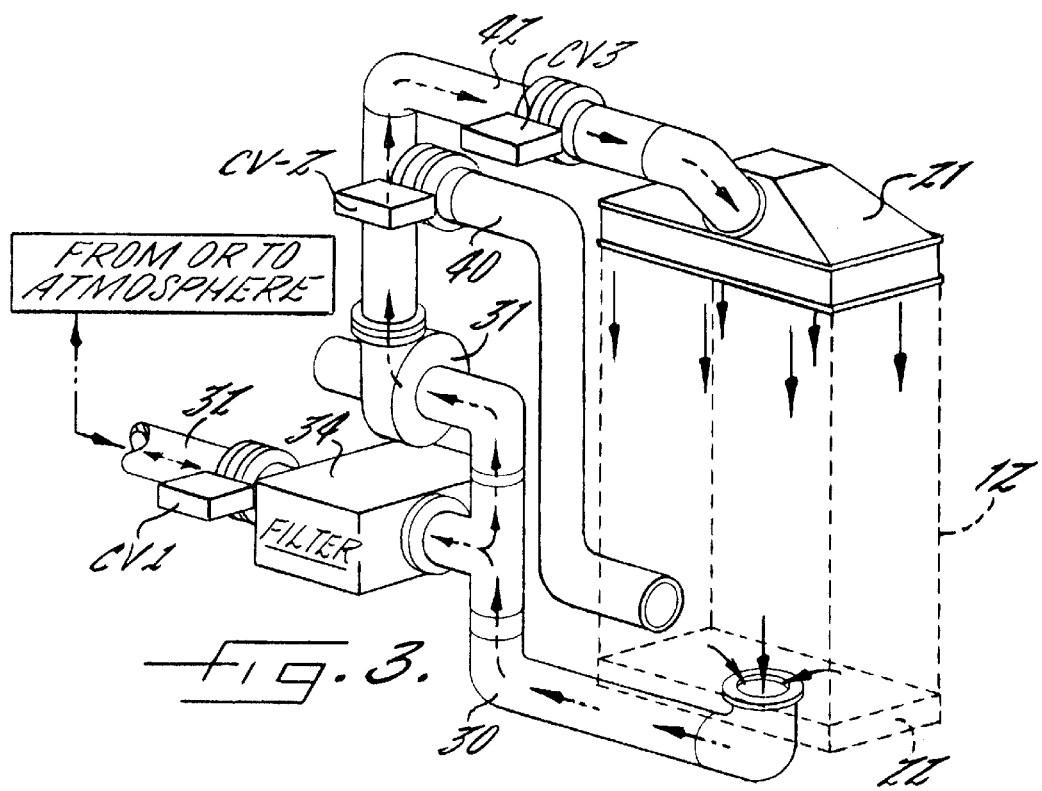

FIG. 3 illustrates the confirmation of the isolation work station in both its normal operation cycle and its purge cycle as described below. During these cycles, valves CV-1 and CV-3 are open, and valve CV-2 is closed. The blower 31 is operated at a speed so as to generate a circulating air flow as illustrated. The fact that the valve CV-1 is open serves to equalize pressure differences resulting from movements of the gloves 20 in the enclosure 12, and normally an insignificant flow enters or leaves through the air inlet duct 32 during these cycles.

Figure 4:
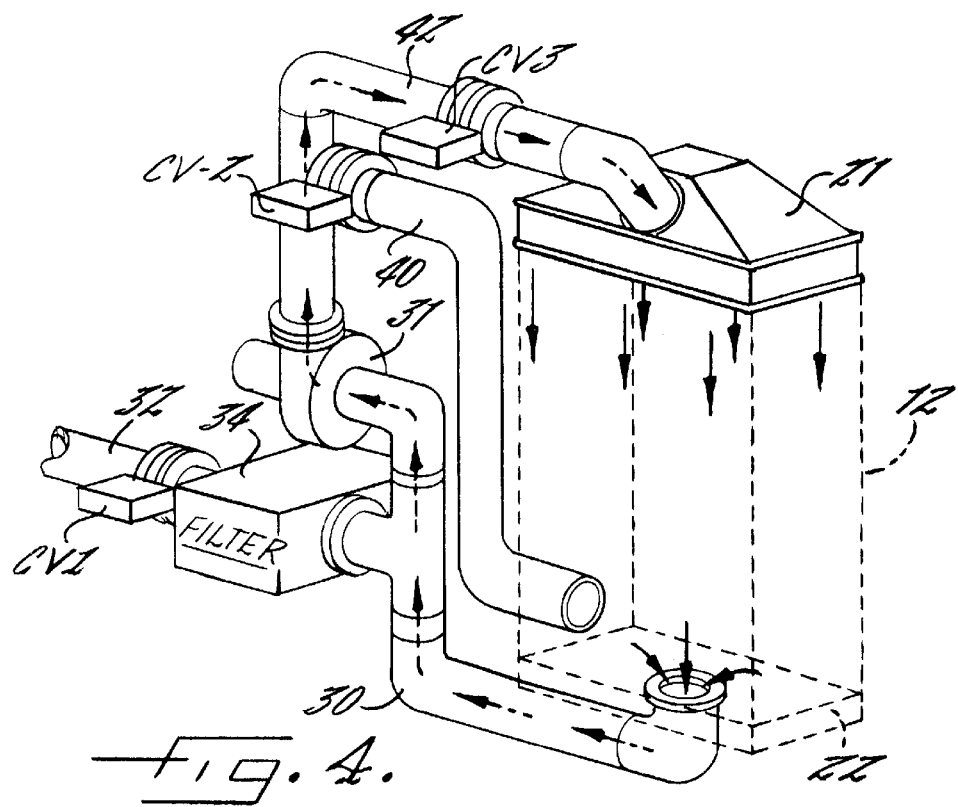

FIG. 4 illustrates the configuration during the pressure decay cycle, which differs from the cycle of FIG. 1 in that the valve CV-1 is closed. The system is thus closed to the atmosphere, and the system is then operated with a positive air pressure so that any leaks in the system may be detected by a pressure drop occurring within the system.

FIG. 5 illustrates the configuration during the sterilization cycle. In this cycle, a sterilant generator as described above is connected to the first and second ports 37, 38. The valve CV-1 is closed, and the valves CV-2 and CV-3 are alternately opened and closed in an opposite sequence. More particularly, when the valve CV-2 is open, the valve CV-3 is closed, and the sterilant bearing airstream is directed directly into the enclosure so as to sterilize the surfaces and products therein. Also, in the illustrated embodiment, the secondary duct 40 is oriented so as to direct the airstream into the enclosure in a circular pattern, which creates a vortex within the enclosure which facilitates contact and sterilization of all surfaces. When the valve CV-3 is open and the valve CV-2 is closed, the sterilant bearing airstream passes through the filter 24 and into the enclosure 12.

Preferably, during the sterilization cycle, the blower speed is increased to about twice its speed during normal operation so that the airstream has a sufficiently short residence time in the filter 24 to preclude significant degradation of the sterilant by the catalyst in the filter.

When sterilization is completed, which typically takes 10–15 minutes, the work station is reconfigured to the mode of FIG. 3, and the purging operation is commenced. All of the air is then circulated through the catalyst bearing filter 24, in this case at a relatively slow speed so as to increase the residence time of the sterilant in the filter. As a result, the catalyst is able to quickly degrade the sterilant into harmless byproducts, such as moisture and oxygen in the case of hydrogen peroxide sterilant. Such purging typically requires 10–15 minutes.

Once normal operation has commenced, it will be understood that the air continues to circulate through the filter 24, which acts to degrade any residual sterilant which is subsequently released by the materials in the enclosure.

As a specific example, the enclosure 12 has a horizontal cross sectional area of about 4.5 square feet, and during the normal operation and purging cycles (FIG. 3), the blower 31 is operated at a speed so as to deliver approximately 100 cfpm through the enclosure, and during the sterilization cycle (FIG. 5), the blower 31 is operated to deliver approximately 200 cfpm through the enclosure.

As indicated above, the filter 24 preferably comprises a sheet of filtering media folded in accordion fashion to form a filter pack 26. In accordance with the present invention, it has been found that the filter may be readily impregnated with a hydrogen peroxide degrading catalyst, by impregnating the media with the smoke of a conventional smoke bomb of the type used to charge a high efficiency air filter during a leak test procedure. As a specific example, the filter 24 in the upper plenum 21 of the work station as described above may have a size of 18×36×5⅞th inches, and a conventional smoke bomb stick is broken in an airstream so that the generated smoke passes through the filter. A suitable smoke bomb stick of this type is manufactured by E. Vernon Hill Incorporated, of Benicia, Calif. and each such stick contains approximately two ml (0.07 fl. oz.) of titanium tetrachloride ($TiCl_4$) in a sealed glass vial. $TiCl_4$ combines with atmospheric moisture to form hydrochloric acid (HCL) along with titanium oxychloride and titanium dioxide. These components are collected on the filtering media, and it is believed that the Titanium dioxide acts as a catalyst for degrading the vaporized hydrogen peroxide which is subsequently passed through the filter into moisture and oxygen.

FIG. 6 illustrates a second embodiment of an isolation work station in accordance with the present invention. In this embodiment, the upper plenum mounts a second high efficiency particulate air filter 24A parallel to and below the catalyst bearing filter 24. The second filter 24A, however, is free of the sterilant degrading catalyst. Also, the secondary duct 40 communicates with the upper plenum at a location between the catalytic filter 24 and the second conventional filter 24A.

In the embodiment of FIG. 6, the valve CV-3 is open during the normal and purge cycles, so that the airstream passes downwardly through both filters. During sterilization, the valve CV-3 is closed and the valve CV-2 is open, as illustrated, whereby the sterilant bearing airstream passes only through the second filter 24A. Thus the sterilant bearing airstream does not pass through the catalyst in the upper filter 24, and any degradation of the sterilant in the upper filter is thereby avoided.

In the drawings and the specification, there has been set forth preferred embodiments of the invention and, although specific terms are employed, the terms are used in a generic and descriptive sense only and not for the purpose of limitation, the scope of the invention being set forth in the following claims.

What is claimed is:

1. A method of purging an isolation work station of residual sterilant after the work station has been sterilized by the introduction of a vaporized sterilant thereinto, and so as to effectively remove the residual sterilant from the work station, and comprising the steps of circulating air along a recirculating path of travel which includes passing the air through a high efficiency particulate air filter and through the work station, with the filter including a catalyst which degrades the sterilant.

2. The method as defined in claim 1 wherein the sterilant is hydrogen peroxide, and wherein said catalyst acts to degrade the hydrogen peroxide into moisture and oxygen.

3. The method as defined in claim 2 wherein said filter comprises a sheet of filtering media folded in accordion fashion upon itself to form a filter pack, with said filtering media being capable of removing at least 99.9% of the submicron sized particles from the air passing therethrough and being impregnated with said sterilant degrading catalyst, and a frame sealably surrounding and supporting the filter pack.

4. The method as defined in claim 3 wherein said sterilant degrading catalyst comprises an oxide of titanium.

5. A method of sterilizing and then purging an isolation work station which comprises an enclosure, a high efficiency particulate air filter sealably mounted above said enclosure, and an air circulation system for circulating an airstream through the filter and then through the enclosure, and with the filter including a sterilant degrading catalyst, and comprising the steps of introducing a vaporized sterilant into the airstream so as to pass through the filter and the enclosure and so as to sterilize the interior of the enclosure, while operating the air circulation system at a relatively high speed so that the airstream has a relatively short residence time in the filter and the sterilant is not significantly degraded by said catalyst, and then purging the sterilant from the airstream and the interior of the enclosure and including operating the air circulation system at a relatively low speed so that the airstream has a relatively long residence time in the filter and the sterilant is rapidly degraded by the catalyst.

6. The method as defined in claim 5 wherein the sterilant is hydrogen peroxide, and wherein the catalyst is an oxide of titanium and acts to degrade the hydrogen peroxide into moisture and oxygen.

7. The method as defined in claim 6 wherein said filter comprises a sheet of filtering media folded in accordion fashion upon itself to form a filter pack, with said filtering media being capable of removing at least 99.9% of the submicron sized particles from the air passing therethrough and being impregnated with said sterilant degrading catalyst, and a frame sealably surrounding and supporting the filter pack.

8. The method as defined in claim 5 wherein the step of introducing a vaporized sterilant into the airstream includes alternately (1) directing the airstream directly into the enclosure so as to bypass the filter, and (2) directing the airstream through the filter and the enclosure.

9. A high efficiency particulate air filter comprising:

a frame having a centrally disposed airflow opening therethrough, and a filter pack sealably mounted in said frame and filling said airflow opening and comprising a sheet of filtering media folded upon itself in accordion fashion, and with said filtering media being capable of removing at least 99.9% of the submicron sized particles from the air passing therethrough and being impregnated with a catalyst in an amount sufficient to efficiently degrade a vaporized sterilant in an airstream passing therethrough.

10. The air filter as defined in claim 9 wherein said catalyst is an oxide of titanium.

11. The method as defined in claim 1 wherein the air circulating step includes circulating the air through the air filter at a predetermined relatively low air speed, and wherein the step of sterilizing the work station includes circulating a sterilant bearing airstream through the air filter at a relatively high air speed so that the airstream has a relatively short residence time in the filter.

12. A method of purging an isolation work station of residual sterilant after the work station has been sterilized by the introduction of a vaporized sterilant thereinto, and so as to effectively remove the residual sterilant from the work station, and comprising the steps of circulating air along a recirculating path of travel which includes passing the air through a high efficiency particulate air filter and through the work station, with the filter including a catalyst which degrades the sterilant, providing a second high efficiency particulate air filter which is free of said catalyst, and periodically circulating a sterilant bearing airstream along a second recirculating path of travel which extends through the second air filter and then through the work station while by-passing the first mentioned air filter.

13. The method as defined in claim 12 wherein the step of circulating air along the first mentioned recirculating path of travel further includes passing the air serially through the first mentioned air filter and then through the second air filter.

* * * * *